US007089684B2

United States Patent
Genier

(10) Patent No.: US 7,089,684 B2
(45) Date of Patent: Aug. 15, 2006

(54) SYSTEM AND METHOD FOR CONVERTING A BIOSOLID SLUDGE TO A PASTEURIZED STAGE FOR USE AS AN ORGANIC FERTILIZER

(75) Inventor: Rejean Genier, Casselman (CA)

(73) Assignee: BRS Agri2000 Ltd., Casselman (CA)

( * ) Notice: Subject to any disclaimer, the term of this patent is extended or adjusted under 35 U.S.C. 154(b) by 253 days.

(21) Appl. No.: 10/809,330

(22) Filed: Mar. 26, 2004

(65) Prior Publication Data

US 2004/0187534 A1 Sep. 30, 2004

(51) Int. Cl.
F26B 3/34 (2006.01)

(52) U.S. Cl. .............................. 34/264; 34/90; 210/603
(58) Field of Classification Search ................. 34/264, 34/90, 58, 61; 210/603
See application file for complete search history.

(56) References Cited

U.S. PATENT DOCUMENTS

| | | |
|---|---|---|
| 3,831,288 A | 8/1974 | Stribling et al. |
| 5,143,626 A | 9/1992 | Nugent |
| 5,145,576 A | 9/1992 | Lataillade |
| 5,389,114 A | 2/1995 | Forder |
| 5,911,885 A | 6/1999 | Owens |
| 6,156,192 A | 12/2000 | Rummler |
| 6,398,921 B1 | 6/2002 | Moraski |
| 6,454,944 B1 * | 9/2002 | Raven ........................ 210/603 |
| 6,719,903 B1 * | 4/2004 | Pressley et al. ............. 210/613 |
| 6,863,826 B1 * | 3/2005 | Sheets ........................ 210/705 |
| 2005/0244328 A1 * | 11/2005 | Schmitz et al. ............. 423/477 |

* cited by examiner

*Primary Examiner*—S. Gravini
(74) *Attorney, Agent, or Firm*—Hoffman, Wasson & Gitler

(57) ABSTRACT

A system for processing biosolids from a sludge pond into fertilizer comprising: a portable dewatering system for removing liquid from sludge, the portable dewatering system having: a collection device for collecting sludge from the sludge pond; a centrifuge for removing liquids from the sludge collected by the collection device to create a biosolids composition; and a transfer device to transfer the biosolids composition from the centrifuge; a transport vehicle for receiving the biosolids composition from the transport device, the transport vehicle transporting the biosolids from the sludge pond to a fixed processing plant; and the fixed processing plant having: a mixer for mixing a stabilizing agent with the biosolids composition to create mixed biosolids; a heating and sterilising system to heat and sterilize the mixed biosolids and for extruding sterilized pellets; and a drying system for drying the pellets, wherein the pellets can be used as fertilizer.

14 Claims, 3 Drawing Sheets

SYSTEM AND METHOD FOR CONVERTING A BIOSOLID SLUDGE TO A PASTEURIZED STAGE FOR USE AS AN ORGANIC FERTILIZER

RELATED APPLICATION

This application claims priority from Canadian Patent Application No. 2,423,581, filed Mar. 27, 2003.

1. Field of the Invention The present invention relates to the sterilisation of biosolids and specifically to the conversion of raw sewage to sterilised fertilizer.

2. Background to the Invention

Raw sewage has become a major problem in the industrialized world. Effluent from raw sewage often fails to meet health and environmental guidelines and this effluent can make its way into water sources such as lakes and rivers. Effluent leaking into water sources poses health risks to people, poisons fish, renders shore areas uninhabitable for aquatic life, and can close beaches to swimmers.

Population growth causes the overburdening of many sewage treatment plants that are already working close to their capacities. The continued population growth in urban areas likely cause these problems to worsen.

Presently, biosolid raw sewage is either brought to a local landfill site where it poses the risk of environmental degradation by seepage into the water table, or is spread onto agricultural land where air pollution is uncontrollable and where the danger of polluting water sources is high.

Attempts have been made to overcome these problems by sterilising biosolids at treatment plants. However, conventional methods generally provide only a low volume of processing using conventional heat sources at a very high cost to treat sewage.

SUMMARY OF THE INVENTION

The present invention seeks to overcome the deficiencies of the prior art by providing a system and method to process a large volume of biosolids using microwave energy at an extruder to sterilise and pasteurise these biosolids. The resultant sterilised pellets can be used for fertilizer without any environmental or health concerns.

The present invention provides a mobile processing plant in which biosolids can be extracted from municipal sludge pits and through a centrifuge be condensed to be transported into a processing plant. The portable system includes a pump, a holding tank with a step cleaner to remove debris, a decanter centrifuge to bring biosolids to a 25% solid concentration, and a conveyor to convey the dewatered solids to a separate transporter such as a truck.

Once the biosolids reach a processing plant, they are mixed with lime and fed into a combination microwave extruder. The combination microwave extruder heats the biosolid to a temperature which will sterilise the biosolids and will extrude the sterilised biosolids into pellets. These pellets are then dried and can be used as fertilizer. The processing plant further includes an air cooling and pumping system for cooling the extruder and for extracting ammonia and water from the exhaust from the biosolids. This air is further dewatered and then pumped through the process pellets in order to dry and keep the processed pellets dry.

The system therefore processes non-treated biosolids through to a treated sterilised fertilizer, and further captures ammonia and water from the exhaust from the biosolids.

The present invention therefore provides a system for processing biosolids from a sludge pond into fertilizer comprising: a portable dewatering system for removing liquid from sludge, said portable dewatering system having a collection device for collecting sludge from said sludge pond, a centrifuge for removing liquids from said sludge collected by said collection device to create a biosolids composition, and a transfer device to transfer said biosolids composition from said centrifuge; a transport vehicle for receiving said biosolids composition from said transport device, said transport vehicle transporting said biosolids from said sludge pond to a fixed processing plant; and the fixed processing plant having a mixer for mixing a stabilizing agent with said biosolids composition to create mixed biosolids, a heating and sterilising system to heat and sterilize the mixed biosolids and for extruding sterilized pellets, and a drying system for drying the pellets, wherein said pellets can be used as fertilizer.

The present invention also provides a portable dewatering system for removing biosolids from a sludge pond, said dewatering system comprising, a collection device to collect sludge from the sludge pond, a holding tank for the sludge collected by said collection device, a centrifuge to dewater sludge from said holding tank, said centrifuge creating a liquid and a biosolids composition, and a transport device to remove said biosolids composition from said centrifuge.

The present invention further provides a microwave extruder for treating biosolids comprising a loading hopper for receiving biosolids, an extruder screw for conveying biosolids from said loading hopper, and a microwave source for heating said biosolids along said extruder screw.

BRIEF DESCRIPTION OF THE DRAWINGS

The present invention will be better understood with reference to the drawings, in which.

DETAILED DESCRIPTION OF THE DRAWINGS

Figure 1:
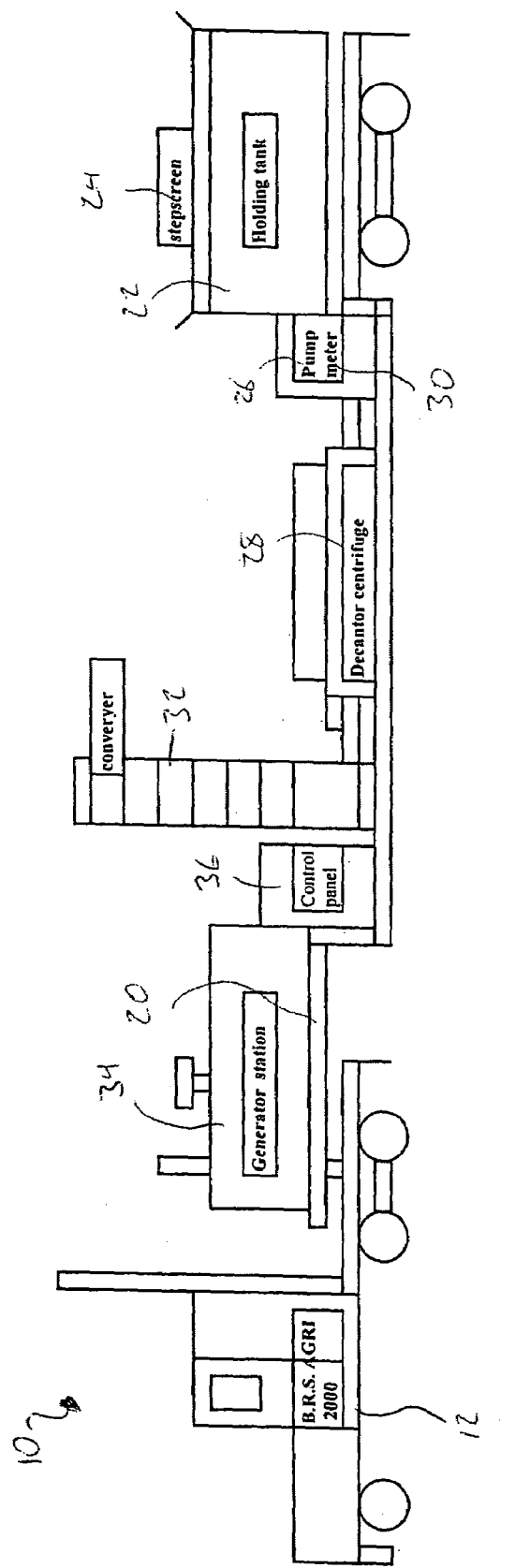
FIG. 1 is a schematic view of a portable dewatering truck of the present invention.

Reference is made to FIG. 1. FIG. 1 shows a portable dewatering system 10 comprising a truck 12 and a trailer 20. The portable dewatering apparatus is driven to a municipal sludge pond in order to dewater sludge within the pond. The object of the portable dewatering apparatus is to create a sludge with a biosolid content of 25%.

A portable pump or a dredger (not shown) is used to collect biowaste from the sludge pond or sewage plant. The portable pump or the dredge is hooked to holding tank 22 using a hose. Holding tank 22 includes a step screen 24 which, through an auger drive, cleans debris from the sludge. This debris is separated and goes into an external container which then is processed according to present methods in the art.

The screened waste product is pumped through pump 26 into decanter centrifuge 28. A meter 30 indicates how many cubic meters of waste are processed through pump 26 in order to provide information for billing purposes.

Decanter centrifuge 28 is used to dewater the waste from holding tank 22. Liquid from decanter centrifuge is either returned to the lagoon or sent to a mechanical processing plant. As one skilled in the art will realize, a different lagoon can be used from the one being processed. A biosolids composition comprising 25% solids is removed from decanter centrifuge 28 using conveyor 32. Conveyor 32 conveys the dewatered biowaste to a separate truck for transport to a processing plant.

The portable pump, auger in step screen 24, pump 26, meter 30, decanter centrifuge 28 and conveyor 32 are all electrically powered. A generation station 34 is further located on portable dewatering apparatus 10 to provide the electricity for these components of the dewatering system. A control panel 36 is used to control the pumps and other electrical apparatus.

One skilled in the art will realize that all of the above components are known separately in the art and suitable selection of these components can be accomplished by one skilled in the art. One example for a decanter centrifuge is the Aldec™ 700 series high performance decanter. However, other decanters and centrifuges can be used.

Figure 2:
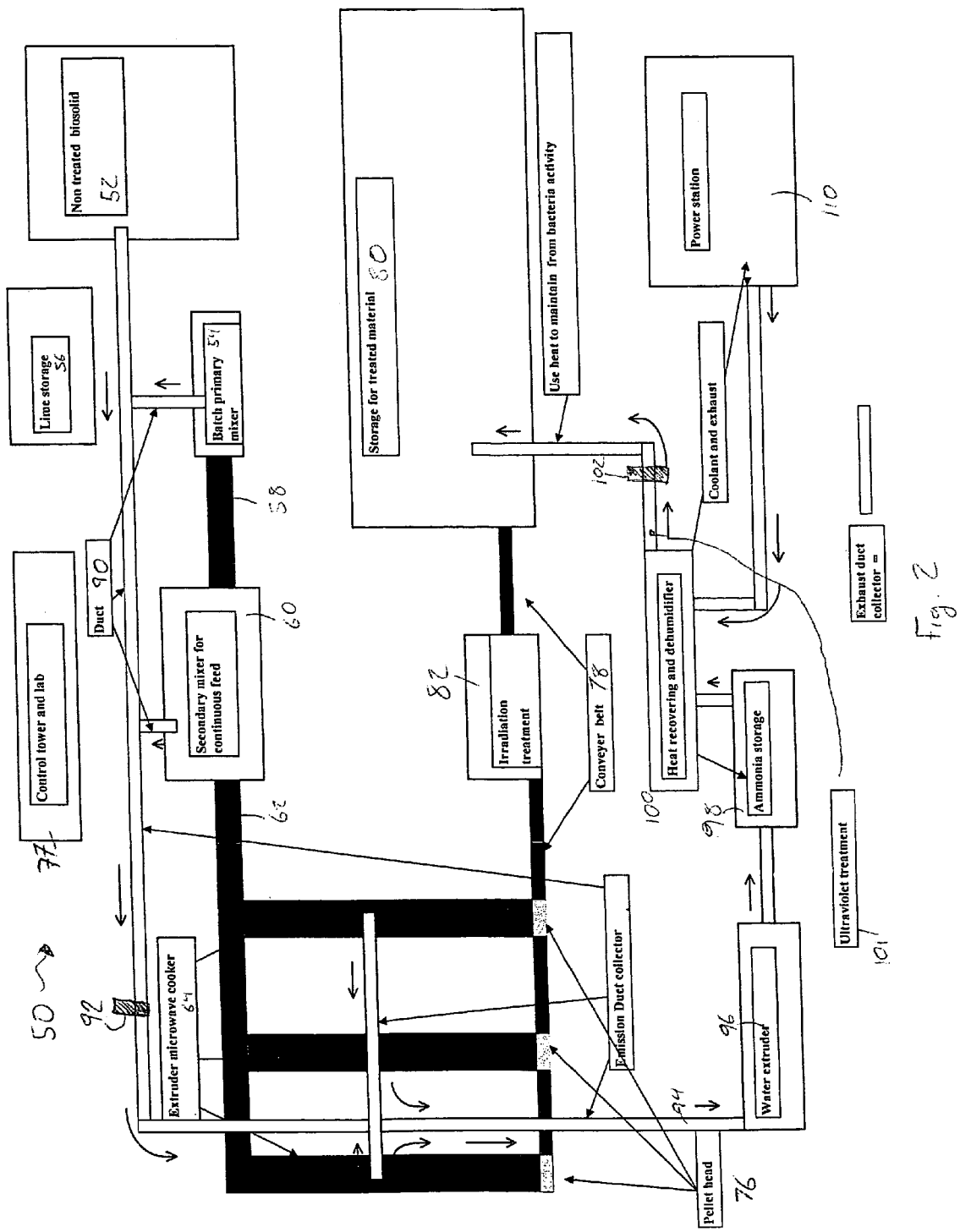
FIG. 2 is a schematic view of the processing plant of the present invention.

Once the sludge is dewatered, it is transported to a processing plant 50. Reference is now made to FIG. 2. The raw biosolids are deposited in a bin 52 for non-treated biosolids. A loader is used to load these non-treated biosolids into batch primary mixer 54. Batch primary mixer 54 mixes the non-treated biolids with lime from a lime storage bin 56 according to preset ratios depending on the type of lime. The mixing of lime into non-treated biosolids is well known in the art. One example of a mixer is a Valmetal™ batch mixer.

A conveyor or auger 58 is used to move the mixed biosolids from batch primary mixer 54 to secondary mixer for continuous feed 60. Secondary mixer for continuous feed 60 is used to constantly keep a batch mixed and to extract mixed batch product from the mixer for further processing. Secondary mixer 60 is larger than batch primary mixer 54, but can also be Valmetal™ batch mixer in a preferred embodiment.

An auger or conveyor 62 is used to convey mixed batch from mixer 60 to microwave extruder 64. In a preferred embodiment, several microwave extruders 64 can be used in parallel in order to increase processing capacity.

Figure 3:
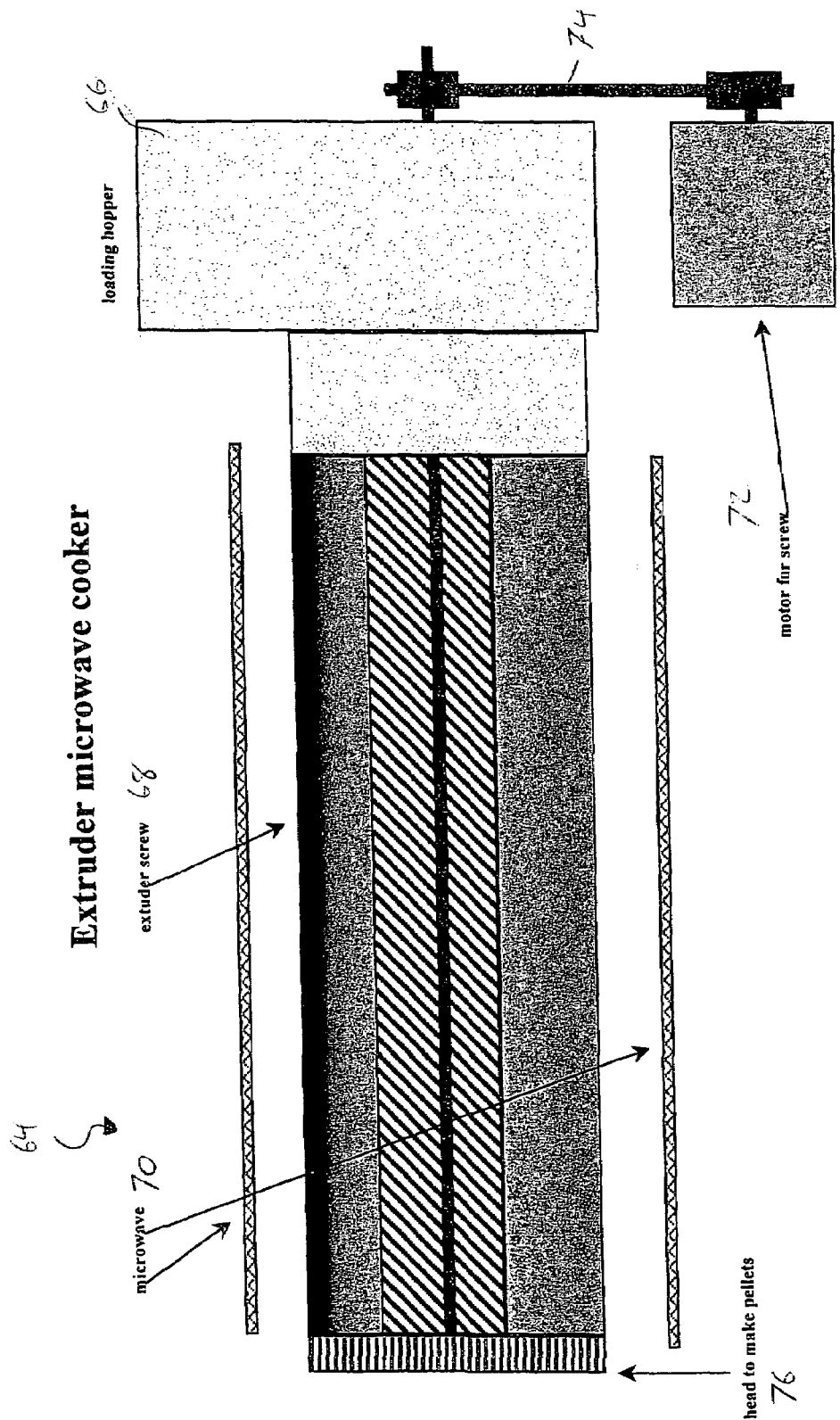
FIG. 3 is a plan view of a cross-section of the microwave extruder of the present invention.

Reference is now made to FIG. 3. FIG. 3 shows a plan view of a microwave extruder that can preferably be used in the present invention. Microwave extruder 64 comprises a loading hopper 66 which receives mixed batch product from auger or conveyor 62. The mixed batch product is conveyed from loading hopper 66 using extruder screw 68. As the mixed batch product is moved along extruder screw 68, microwaves from microwave source 70 are used to heat the batch product. This both aids in extrusion and is used to sterilise the mixture. In a preferred embodiment, the system heats the mixed batch product to a temperature to kill all bacteria and parasites. As one skilled in the art will realize, the use of microwaves presents the advantage that less energy is required to bring the mixture up to a heat sufficient for this purpose. Further, the pressure in the extruder also aids in the sterilisation process, thus creating significant advantages in the heating and processing of biowastes.

The advantage of the extruder microwave cooker in the present invention is that heating occurs at least five times faster than using conventional heating methods, and therefore at least five times the processing rate can be accomplished.

Extruder screw 68 is powered by motor 72 which through a belt 74 is used to turn extruder screw 68.

A control tower and lab 77 can be used to monitor the temperature along the extruder, and individual areas within the extruder can be controlled individually in order to increase or decrease the microwave irradiation of the biosolids, thereby increasing or decreasing the amount of energy supplied to the biosolids to optimize the processing thereof.

At the end of extruder screw 68 is a head 76 which is used to make pellets for fertilizer. The sterilised batch mixture is forced through head 76 to create pellets.

As best seen in FIG. 2, once pellets have been extruded from pellet head 76, a conveyor belt 78 conveys the pellets to a storage bin 80 in which the pellets can be stored until they are ready to be transported. An optional irradiation or microwave treatment 82 can further be added along conveyor belt 78 in order to ensure that sterilisation has in fact occurred.

Processing plant 50 also isolates all gases and emissions from the biosolids. These are used for a variety of purposes, including the cooling of microwave extruder 64, recovery of ammonia, and drying of the pellets in storage bin 80. A series of ducts 90 are connected to non-treated biosolids bin 52, batch primary mixer 54, and secondary batch mixer 60. A fan 92 pulls these gases from ducts 90 and pushes them into microwave extruder 64. In microwave extruder 64, these gases are used to cool the extruder to prevent overheating, with the secondary benefit that the air is heated which facilitates the extraction of ammonia. The emissions from microwave extruder 64 are collected in duct collector 94 and are sent to water extruder 96.

Water extruder 96 is used to remove ammonia and water from the emissions and to store these for further processing and to recover ammonia. Ammonia is stored in ammonia storage 98.

The gases are sent from the water extruder into heat recover and dehumidifier 100 which further dries the gases. These warm dry gases are then sent using a fan 102 under storage bin 80, and the gases are allowed to flow through the pellets stored within storage bin 80. This further dries the pellets.

An ultraviolet treatment 101 is used between heat recovery and dehumidifier 100 and fan 102 to further sterilise the exhaust gases by eliminating these gases with an ultraviolet light. This type of sterilisation is well known in the art.

All of the components within the processing plant 50 are electrical, and a power station 110 is used to provide power to all of these components. The exhaust from power station 110 can further be processed by first sending it through heat recovery and dehumidifier 100, which removes excess water.

The exhaust gases are then blown using fan 102 through the pellets stored in storage bin 80. By projecting the exhaust upwards through the pellets in storage bin 80, these exhaust fumes can be filtered through the biosolid pellets to produce a clean system with no pollution.

As one skilled in the art will appreciate, this system converts raw biowastes into a fertilizer and further can be used to recover ammonia.

The above described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following claims.

We claim:

1. A system for processing biosolids from a sludge pond into fertilizer comprising:
   (a) a portable dewatering system for removing liquid from sludge, said portable dewatering system having:

a collection device for collecting sludge from said sludge pond;

a centrifuge for removing liquids from said sludge collected by said collection device to create a biosolids composition; and a transfer device to transfer said biosolids composition from said centrifuge;

(b) a transport vehicle for receiving said biosolids composition from said transport device, said transport vehicle transporting said biosolids from said sludge pond to a fixed processing plant; and (c) the fixed processing plant having:

a mixer for mixing a stabilizing agent with said biosolids composition to create mixed biosolids;

a heating and sterilising system to heat and sterilize the mixed biosolids and for extruding sterilized pellets; and a drying system for drying the pellets, wherein said pellets can be used as fertilizer.

2. The system of claim 1, wherein said portable dewatering system is mounted on a truck.

3. The system of claim 1, wherein said collection device is a pump.

4. The system of claim 1, wherein said collection device is a dredge.

5. The system of claim 3, wherein said transfer device is a conveyor.

6. The system of claim 5, wherein said portable dewatering system, further comprising a generator to power said pump, centrifuge and conveyor.

7. The system of claim 6, wherein said portable dewatering system further comprises a holding tank for holding sludge collected by said pump.

8. The system of claim 7, wherein said portable dewatering system further comprising a step screen between said holding tank and said centrifuge to remove debris from said sludge.

9. The system of claim 8, wherein said step screen includes an auger drive.

10. The system of claim 1, wherein said biosolids composition includes 25% solids.

11. The system of claim 1, wherein said heating and sterilizing system is a microwave extruder.

12. The system of claim 11, wherein said microwave extruder includes:

a loading hopper for receiving mixed biosolids;

an extruder screw for conveying mixed biosolids from said loading hopper;

a microwave source for heating said mixed biosolids along said extruder screw.

13. The system of claim 12, wherein said processing plant further includes an ultraviolet treatment device for treating said mixed biosolids.

14. The system of claim 13, wherein said processing plant further includes an ammonia recovery device to recover ammonia from said mixed biosolids.

* * * * *